(12) United States Patent
Castellanos

(10) Patent No.: US 7,232,419 B2
(45) Date of Patent: Jun. 19, 2007

(54) ENCLOSURE WITH CAM ACTION SNAP RELEASE

(75) Inventor: Rafael A. Castellanos, Roselle, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 440 days.

(21) Appl. No.: 10/365,210

(22) Filed: Feb. 11, 2003

(65) Prior Publication Data

US 2003/0181849 A1 Sep. 25, 2003

Related U.S. Application Data

(63) Continuation-in-part of application No. 10/074,532, filed on Feb. 11, 2002.

(51) Int. Cl.
*A61M 1/00* (2006.01)

(52) U.S. Cl. .................. 604/29; 604/533; 206/438
(58) Field of Classification Search ............... 604/43, 604/28, 403, 6.15, 29, 6.16, 533, 326, 905, 604/110; 128/200.23; 210/646; 206/438
See application file for complete search history.

(56) References Cited

U.S. PATENT DOCUMENTS

| | | | |
|---|---|---|---|
| 3,447,161 A | 6/1969 | Weikel | |
| 3,468,447 A * | 9/1969 | Smalley | ................... 215/295 |
| 3,858,580 A | 1/1975 | Ogle | |
| 3,986,508 A | 10/1976 | Barrington | |
| 4,201,208 A | 5/1980 | Cambio, Jr. | |
| 4,334,551 A | 6/1982 | Pfister | |
| 4,354,490 A | 10/1982 | Rogers | |
| 4,432,764 A | 2/1984 | Lopez | |
| 4,432,766 A | 2/1984 | Bellotti et al. | |
| 4,457,749 A | 7/1984 | Bellotti et al. | |
| 4,511,359 A | 4/1985 | Vaillancourt | |
| 4,526,572 A | 7/1985 | Donnan et al. | |
| 4,551,146 A | 11/1985 | Rogers | |
| 4,580,816 A | 4/1986 | Campbell et al. | |
| 4,610,469 A | 9/1986 | Wolff-Mooij | |
| 4,617,012 A | 10/1986 | Vaillancourt | |

(Continued)

FOREIGN PATENT DOCUMENTS

CA  1256343 A1  6/1989

(Continued)

OTHER PUBLICATIONS

International Search Report for International Patent Application No. PCT/US2005/038424 that corresponds to the present application and of which the references cited above as cited therein.

*Primary Examiner*—Nicholas Lucchesi
*Assistant Examiner*—Christopher D. Koharski
(74) *Attorney, Agent, or Firm*—Joseph P. Reagen; Bell, Boyd & Lloyd LLC

(57) ABSTRACT

Apparatuses and methods for maintaining sterile connections during, for example, dialysis therapy. The present invention provides a container for a medical device and a lid therefore. The lid and the container are configured for an easy snap release using a cam-follower system. The invention also provides a method for using an assembly of the container, lid and a medical device within the container to maintain sterile connections.

25 Claims, 8 Drawing Sheets

U.S. PATENT DOCUMENTS

| | | | |
|---|---|---|---|
| 4,623,327 A | | 11/1986 | Mahurkar |
| 4,624,664 A | | 11/1986 | Peluso et al. |
| 4,655,762 A | | 4/1987 | Rogers |
| 4,675,004 A | | 6/1987 | Hadford et al. |
| 4,701,159 A | | 10/1987 | Brown et al. |
| 4,770,652 A | | 9/1988 | Mahurkar |
| 4,810,241 A | * | 3/1989 | Rogers .................. 604/28 |
| 4,816,221 A | | 3/1989 | Harvey et al. |
| 4,842,582 A | | 6/1989 | Mahurkar |
| 4,895,570 A | | 1/1990 | Larkin |
| 4,941,517 A | | 7/1990 | Galloway |
| 4,983,161 A | * | 1/1991 | Dadson et al. ............ 604/28 |
| 4,985,034 A | | 1/1991 | Lipton |
| 5,009,636 A | | 4/1991 | Wortley et al. |
| 5,100,394 A | | 3/1992 | Dudar et al. |
| 5,137,524 A | | 8/1992 | Lynn et al. |
| 5,188,593 A | | 2/1993 | Martin |
| 5,190,534 A | * | 3/1993 | Kendell .................. 604/6.16 |
| 5,211,638 A | | 5/1993 | Dudar et al. |
| 5,242,425 A | | 9/1993 | White et al. |
| 5,263,930 A | | 11/1993 | Ensminger |
| 5,269,764 A | | 12/1993 | Vetter et al. |
| 5,279,605 A | | 1/1994 | Karrasch et al. |
| 5,324,128 A | * | 6/1994 | Gueret .................. 401/126 |
| 5,378,230 A | | 1/1995 | Mahurkar |
| 5,393,101 A | | 2/1995 | Matkovich et al. |
| 5,431,280 A | | 7/1995 | Bryant |
| 5,437,650 A | | 8/1995 | Larkin et al. |
| 5,456,675 A | | 10/1995 | Wolbring et al. |
| 5,489,278 A | | 2/1996 | Abrahamson |
| 5,501,676 A | | 3/1996 | Niedospial et al. |
| 5,507,733 A | | 4/1996 | Larkin et al. |
| 5,571,093 A | | 11/1996 | Cruz et al. |
| 5,620,427 A | | 4/1997 | Werschmidt et al. |
| 5,694,978 A | | 12/1997 | Heilmann et al. |
| 5,743,892 A | | 4/1998 | Loh et al. |
| 5,776,116 A | | 7/1998 | Lopez et al. |
| 5,782,808 A | | 7/1998 | Folden |
| 5,810,398 A | | 9/1998 | Matkovich |
| 6,027,489 A | | 2/2000 | Galato |
| 6,079,432 A | | 6/2000 | Paradis |
| 6,096,011 A | * | 8/2000 | Trombley et al. ............ 604/256 |
| 6,105,770 A | * | 8/2000 | Vasudeva .................. 206/378 |
| 6,183,465 B1 | | 2/2001 | Meier et al. |
| 6,183,467 B1 | | 2/2001 | Shapeton et al. |
| 6,311,838 B1 | | 11/2001 | Johnson et al. |
| 6,358,241 B1 | | 3/2002 | Shapeton et al. |
| 6,367,640 B1 | | 4/2002 | Julian |
| 6,585,695 B1 | * | 7/2003 | Adair et al. ............ 604/183 |
| 2002/0010437 A1 | | 1/2002 | Lopez et al. |
| 2003/0006610 A1 | | 1/2003 | Werth |
| 2003/0184090 A1 | | 10/2003 | Guala |
| 2004/0087986 A1 | | 5/2004 | Ott |
| 2004/0111078 A1 | | 6/2004 | Miyahara |
| 2004/0238776 A1 | | 12/2004 | Peters et al. |

FOREIGN PATENT DOCUMENTS

| | | |
|---|---|---|
| DE | 390140 | 2/1924 |
| EP | 0 092 528 A1 | 10/1983 |
| EP | 0 554 722 A1 | 8/1993 |
| EP | 833679 A1 | 4/1998 |
| EP | 851778 A1 | 7/1998 |
| EP | 0896827 | 2/1999 |
| EP | 1243280 | 9/2002 |
| EP | 1331020 | 7/2003 |
| GB | 894854 | 4/1962 |
| GB | 927151 | 5/1963 |
| GB | 2067075 A | 7/1981 |
| GB | 2343723 | 5/2000 |
| JP | 9-192216 A2 | 7/1997 |
| JP | 10-248924 A2 | 9/1998 |
| JP | 11-057419 A2 | 3/1999 |
| JP | 11-128359 A2 | 5/1999 |
| JP | 2000014772 A2 | 1/2000 |
| JP | 2000140099 A2 | 5/2000 |
| WO | 83/00812 A1 | 3/1983 |
| WO | WO94/23775 | 10/1994 |
| WO | 95/15194 A1 | 6/1995 |
| WO | 01/85249 A1 | 11/2001 |
| WO | WO2004/033023 | 4/2004 |
| WO | WO2004/071557 | 8/2004 |

* cited by examiner

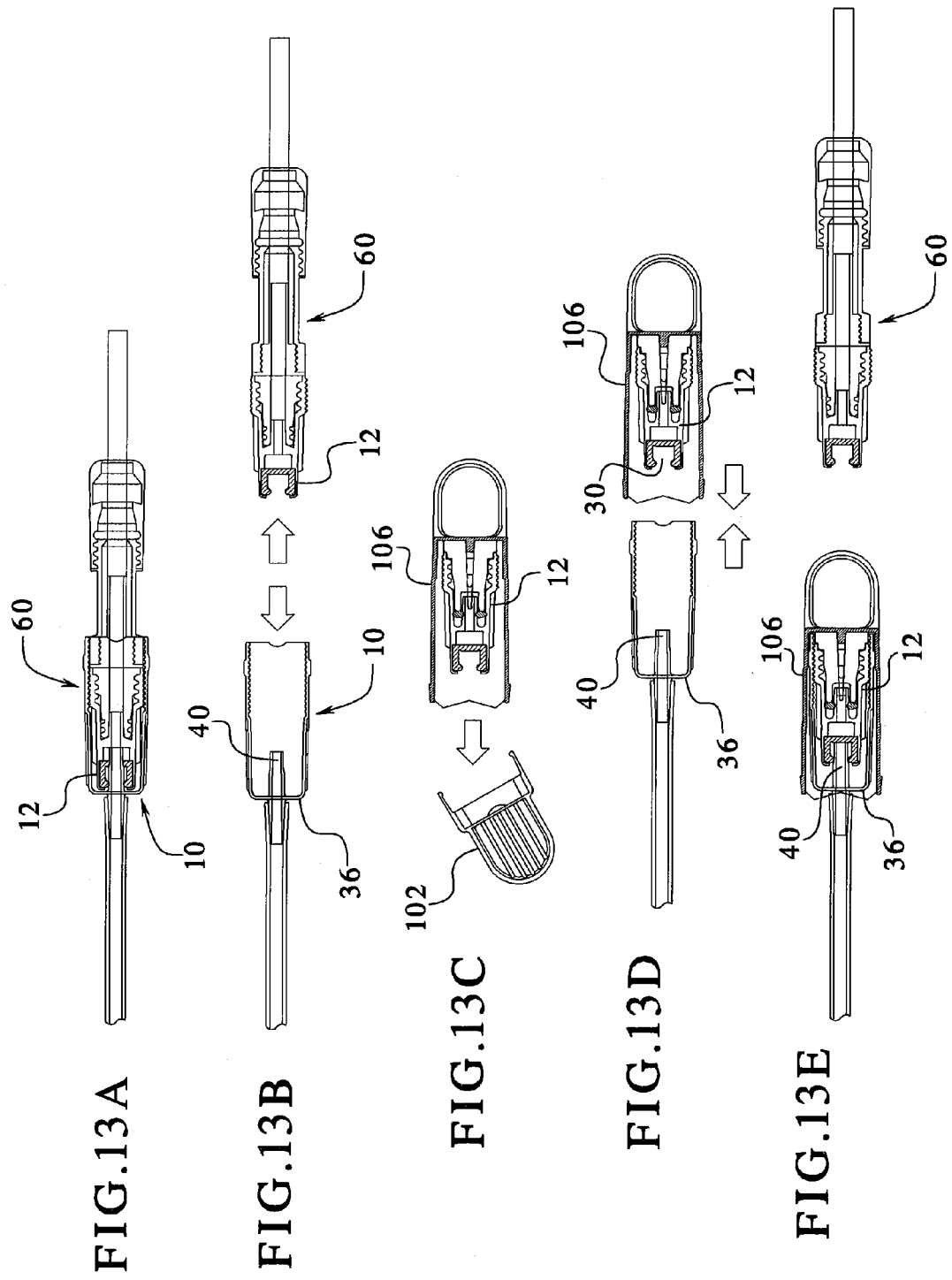

ENCLOSURE WITH CAM ACTION SNAP RELEASE

CROSS-REFERENCE TO RELATED APPLICATIONS

This application is a continuation-in-part of U.S. patent application Ser. No. 10/074,532, filed on Feb. 11, 2002 entitled "Dialysis Connector and Cap Having an Integral Disinfectant" the entire disclosure of which is hereby incorporated by reference.

BACKGROUND OF THE INVENTION

The present invention relates generally to medical treatments. More specifically, the present invention relates to containers for medical connectors for use in medical treatments, such as Peritoneal Dialysis ("PD").

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

PD uses a dialysis solution or dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs by diffusion and osmosis because there is an osmotic gradient across the peritoneal membrane. The spent dialysate is drained from the patient's peritoneal cavity to remove the waste, toxins and water from the patient. New dialysate replaces the spent dialysate and the process repeats.

During dialysis therapy, a dialysis fluid exchange generally includes draining spent dialysis fluid from the peritoneal cavity and filling the peritoneal cavity with fresh dialysate. Keeping track of the amounts or volumes of dialysis solution drained from and supplied to the peritoneal cavity is important for proper dialysis therapy. A typical amount of dialysate solution drained from and supplied to the peritoneal cavity of an adult during an exchange can be roughly two to three liters. Dialysis fluid exchanges have been performed manually, usually by the patient, or automatically, by an automated dialysis machine.

In PD, a catheter is implanted into the peritoneal cavity of the patient. A dialysis solution ("dialysate") is introduced through the catheter into the peritoneal cavity of a patient. In the manual PD technique, known as Continuous Ambulatory Peritoneal Dialysis ("CAPD"), a container of the dialysate connects to a connector, which in turn couples to the catheter. To start the flow of dialysate into the peritoneal cavity, a clamp on a tube connecting the container to the connector is loosened or a valve is opened. In many cases the container is located vertically above the patient and gravity fed into the peritoneal cavity.

In the Automated Peritoneal Dialysis technique ("APD"), dialysis machines use one or more fluid pumps to perform the dialysate exchanges. The pump pumps spent dialysate fluid out of the peritoneal cavity during the drain mode and pumps dialysate into the cavity during the fill mode.

In either PD technique, once the dialysate reaches the patient, dialysis of urea, toxic waste and the like takes place between the dialysate and the blood passing through blood vessels in the peritoneum, which is the lining of the peritoneal cavity. The dialysate remains in the peritoneal cavity for several hours. Thereafter, the dialysate is removed from the peritoneal cavity carrying with it diffused breakdown products from the blood. In CAPD, one method for removing the spent dialysate is to lower the dialysate container outside of the body and let the dialysate drain into the container.

The spent container is disconnected and discarded, wherein a new container of dialysate fluid is attached and the process is repeated. This process may be repeated several times or continuously repeated. Because many patients perform the PD (CAPD or APD) procedure themselves, it is important that the connector which connects the dialysate container to the catheter is easy to use and provides a secure connection.

A frequent problem that occurs with PD is peritoneal infection or peritonitis which can readily occur given the repeated disconnecting and reattaching of the dialysate containers. Peritonitis can result if connections are made between the peritoneal catheter and the connector communicating with the dialysis container in a manner that permits even a very small number of microorganisms to enter the catheter. The microorganisms will be flushed into the peritoneal cavity. Peritonitis can occur even when extreme caution is observed in making and unmaking the connections. Peritonitis can be painful and can temporarily diminish the hydraulic permeability of the peritoneal membrane, rendering the renal treatment less successful.

Methods to prevent peritonitis have included thoroughly cleansing the connector and the tube connecting the dialysate container before the connection is made. For instance, the connector can be immersed in povidone iodine, betadine or other type of disinfectant. These methods however are messy, time consuming, effort consuming, inconsistent and may be subject to overkill in order to achieve consistently effective results. Hospital workers, as another precaution, typically wear sterile rubber gloves to prevent or guard against any possible peritoneal invasion of bacteria. However, the spread of contamination can still occur due to, for example, a cut in the glove or other like condition.

Accordingly, the frequent connections that must be made and broken between the catheter residing in the peritoneal cavity and a succession of dialysate containers has created a need to ensure the sterilization of connectors used in performing CAPD and APD. Attempts have been made to saturate an absorbent material with disinfectant and dispose the material in the connector such that it contacts the tube/connector interface. A need still exists however to improve the efficiency, effectiveness and cost of providing sterile connections for PD.

A continuing need therefore exists to provide a simple and effective method and apparatus for performing PD, including CAPD and APD both in hospitals and at a patient's home.

SUMMARY OF THE INVENTION

The present invention relates to a connector and a cap that are easily and readily attachable to a dialysate container and a catheter inserted into a patient's peritoneal cavity. The connector and the cap enable the dialysate to be readily transported between the container and the peritoneal cavity while minimizing the potential of contamination therein due to, for example, handling during use.

To this end, in an embodiment of the present invention, a container for a medical device is provided which includes a body defining a passage and a bottom surface and with an opening opposite the bottom surface. The bottom surface includes an integrally formed securing mechanism for retaining the medical device securely in the body of the container. In a preferred embodiment, the integrally formed securing mechanism engages an interior surface of the medical device so that the device is held securely within the container. The container of the present invention also includes a lid. The lid and the body of the container are configured to provide an easy snap release of the lid from the body using a cam-follower action or cantilever action.

Preferably, the container body will include a collar which defines an opening which will have a continuous cam edge geometry. The collar is designed to be engaged by the lid with a snap mechanism. The lid includes a follower for engaging the cam edge geometry of the collar, so that turning the lid will push the lid away from the container. In an exemplary embodiment, the container body further includes an integrally formed handle which is preferably attached to the bottom surface of the body. The handle allows the container to be used in such a fashion that the patient or user's hands do not come in contact with the medical device housed therein, thus reducing the risk of contamination to the device.

In a preferred embodiment, the container further includes a medical device housed therein. Preferably, the medical device is a cap for use in a connector making a resealable fluid path. In another embodiment, the medical device further includes a seal disposed within an interior surface, the seal maintaining a disinfectant. Preferably, the disinfectant comprises povidone iodine.

In another embodiment, the lid for the container includes a downwardly extending projection for engaging and holding the medical device in place. In still yet another embodiment, the lid includes a tip protector for engaging a slit septum of the medical device. In a preferred embodiment, the lid includes an integrally formed handle for allowing the patient or user to easily turn and remove the lid from the container.

The present invention also provides a method of maintaining a sterile connection for a dialysate line. The method includes the steps of providing a first member in fluid communication with a dialysate line and a second member in fluid communication a patient line, wherein the first member and second member are connected. The first member and the second member are then disconnected. A container for a medical device is then provided. The container includes a lid, and a medical device disposed within the container. The lid is removed from the container and the first member is inserted into the container simultaneously inserting the medical device into the first member thus protecting the member from contamination. Preferably, the lid of the container has an easy snap release using cam-follower action.

In an embodiment, the medical device further includes a seal disposed within an interior surface, the seal maintaining a disinfectant. The method may also include the step of pulling away the container for the medical device from the medical device whereby the medical device is left inside the first member. After removing the container from the first member the second member is reconnected to the first member and the medical device connected thereto.

In an embodiment, connecting the second member to the first member and the medical device connected thereto displaces the seal and releases the disinfectant.

The present invention also provides a method for providing peritoneal dialysis. The method includes the steps of providing a first member in fluid communication with a dialysate container, a second member in fluid communication with a peritoneal cavity of a patient, the first member and second member being connected. A container for a medical device is provided, the container includes a lid, and a medical device disposed within the container. The first member and the second member are then disconnected. The lid is then removed from the container and the first member is inserted into the container simultaneously inserting the medical device into the first member thus protecting the first member from contamination. The container is pulled away from the medical device, leaving the medical device connected to the first member. The second member is reconnected to the first member and the medical device connected thereto. The peritoneal cavity is then filled with an amount of fresh dialysate fluid.

In a preferred embodiment, the lid of the container has an easy snap release using a cam-follower system. In another embodiment, the medical device further includes a seal disposed within an interior surface, the seal maintaining a disinfectant.

In an embodiment, connecting the second member to the first member and the medical device connected thereto displaces the seal and releases the disinfectant.

Additional features and advantages of the present invention are described in, and will be apparent from, the following Detailed Description of the Invention and the Figures.

BRIEF DESCRIPTION OF THE FIGURES

FIG. 13A is a schematic sectional view illustrating one step for using the container of the present invention to maintain a sterile connection during treatment.

FIG. 13B is a schematic sectional view illustrating another step for using the container and device of the present invention to maintain a sterile connection during treatment.

FIG. 13C is a schematic sectional view illustrating a further step for using the container and device of the present invention to maintain a sterile connection during treatment.

FIG. 13D is a schematic sectional view illustrating still another step for using the container and device of the present invention to maintain a sterile connection during treatment.

FIG. 13E is a schematic sectional view illustrating still another step for using the container and device of the present invention to maintain a sterile connection during treatment.

DETAILED DESCRIPTION OF THE INVENTION

The present invention provides a connector and a cap therefore that includes a disinfectant for any system requiring a connection, such as a connection of a first length of tubing or other conduit to a second length of tubing or other conduit, such as for PD. The present invention provides a safe and easy connection and method for introducing a disinfectant for a user/patient. The connector and cap therefore do not create a mess and do not make the user/patient perform special handling in order not to spill the disinfectant contained therein.

The method and apparatus for the present invention can be used to perform Continuous Ambulatory Peritoneal Dialysis ("CAPD") and Automated Peritoneal Dialysis ("APD"), collectively referred to herein as Peritoneal Dialysis ("PD"). It should be appreciated, however, that the connector and cap and method for using same can be used in a variety of other applications, particularly applications that insert a medical fluid into the body of a patient.

Figure 1A:
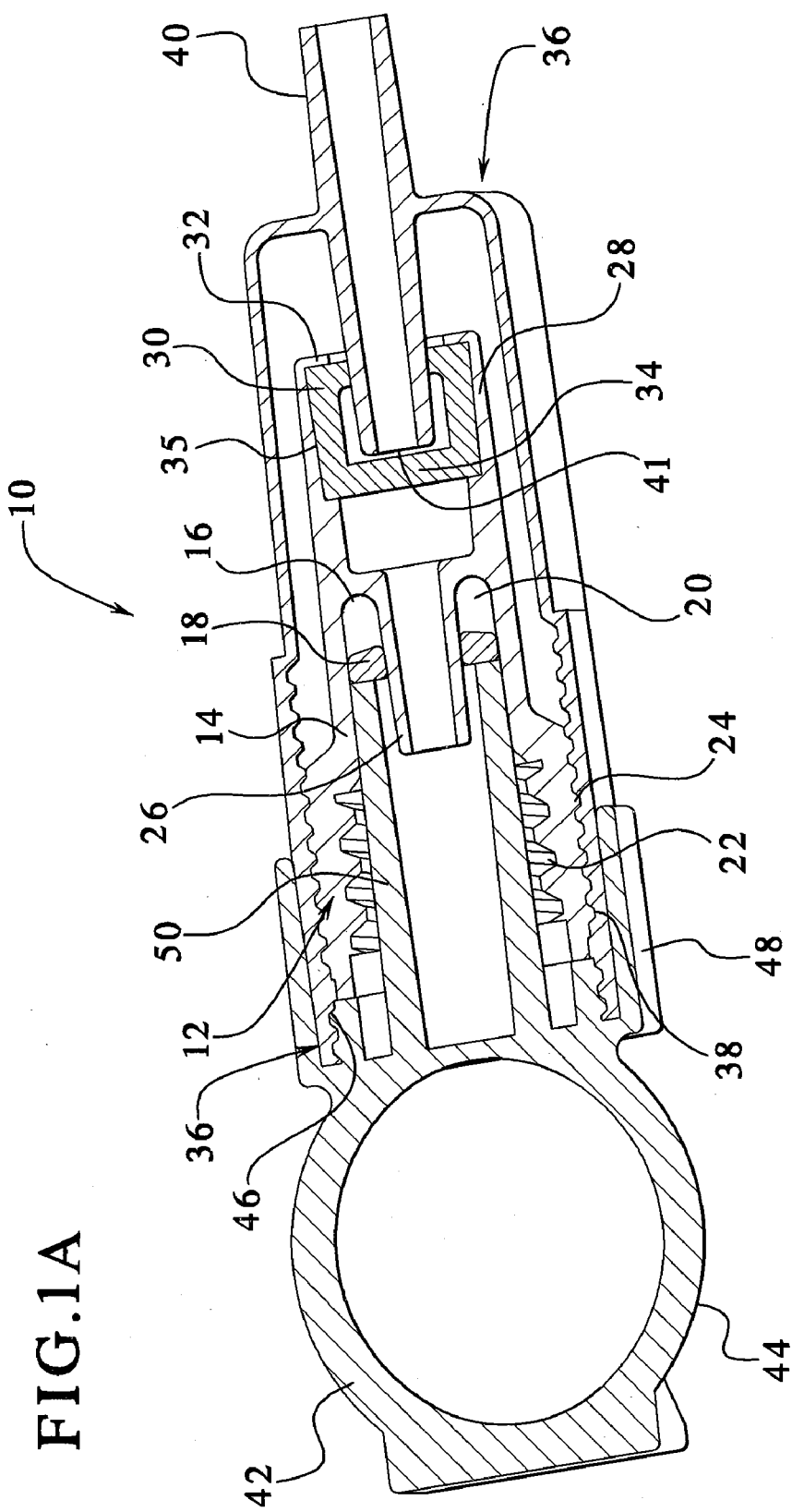
FIG. 1A is a perspective view of one embodiment of the dialysis connector and cap therefore of the present invention.
Figure 1B:
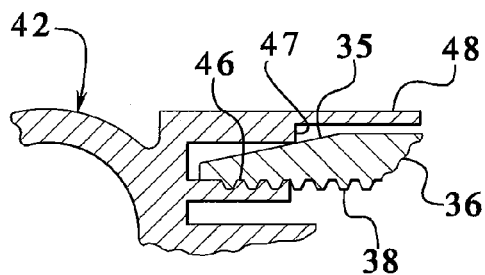
FIG. 1B is a schematic sectional view showing an embodiment of an interface between the shell and the tip protector.
Figure 1C:
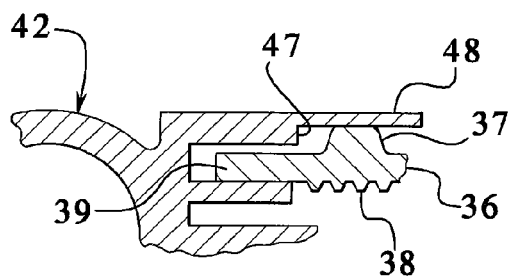
FIG. 1C is a schematic sectional view showing another embodiment of an interface between the shell and the tip protector.

Referring now to the figures, and in particular to FIGS. 1A to 1C, a connector 10 of the present invention is illustrated.

FIG. 1A illustrates that the connector 10 includes a cap 12. Generally, the components of the present invention, including the cap 12, are made of a plastic material such as polyethylene, polypropylene, nylon, polystyrene, polyester, PVC, a blend of various plastics or any other plastic or synthetic material that is capable of being washed and sterilized or substantially sterilized. As is illustrated below, certain components of the connector 10 seal to other components. These sealing components are generally made from compressible materials such as compressible rubber, e.g., silicone or the like.

The components of the connector 10 are constructed into desired shapes via any known method for producing plastic or rubber pieces, such as a molding process, e.g., an injection molding process. The compressible or rubber pieces may alternatively be cut and/or stamped from a larger piece of the compressible or rubber material. In alternative embodiments, one or more of the components, i.e., the plastic components, may alternatively be constructed from a metal, e.g., a noncorrosive metal such as stainless steel or aluminum, and may be formed via any known method of forming or stamping same.

The cap 12 includes a body 14 that is injection molded or blow molded to define a desired shape. Although FIG. 1A shows one embodiment of the connector 10 and the cap 12, the body 14 of the cap 12 may be made in a variety of different shapes and sizes to mate with and/or work with various systems for introducing medical fluids into a patient. The various systems can be provided by other manufacturers or by the assignee of this invention. In one embodiment, the body 14 defines the following components or features.

The body 14 defines at least one receptacle 16. The receptacle 16 is a well or other liquid containing shape that encompasses a void except for a sealable side. The body 14 can define a variety of different receptacles 16; however, FIG. 1A shows an embodiment wherein the body 14 defines a single receptacle 16. A seal 18 encloses or caps off the receptacle 16. The seal 18 in an embodiment is a crosslinked elastomeric seal made from silicone. The seal may alternatively be made from any other type of rubber or compressible material such as neoprene, vinyl, viton, buna-n, butyl, EPDM, latex or the like.

The seal 18 can be made from solid or sponge rubber. In an embodiment, the seal 18 may be clear so that the user or patient can see a disinfectant 20 housed between the seal and the receptacle 16. In an embodiment, the seal 18 is coated with or impregnated with a disinfectant, which acts to further sterilize the connector 10.

In an embodiment, the seal 18 compresses against the walls of the receptacle 16, so that the disinfectant 20 residing within the receptacle 16 in any suitable form and/or manner cannot initially escape, even if the cap 12 of the connector 10 is turned so that the seal 18 faces downward and even if the patient or user moves, manipulates, shakes or otherwise causes the disinfectant 20 to move within the receptacle 16.

In an embodiment, the seal 18, compressed within the walls of the receptacle 16, is translatable so that the seal 18 can move towards an end of the receptacle 16. The method for translating the seal 18 is set forth in detail below in connection with FIGS. 3 to 7. In an alternative embodiment, the seal 18 is thin or otherwise frangible, e.g., is constructed from a thin plastic or metal-coated plastic sheet. The sheet is designed to rip when the patient or user applies pressure to the sheet, wherein the disinfectant flows through the ruptured sheet of the seal 18. In the alternative embodiment, the seal 18 would not compress against the walls of the receptacle 16; rather, a suitable adhesive would be used to secure the seal 18 to the receptacle 16, or the seal 18 could be adhered to the receptacle 16 via a known heat-shrinking or heating process.

The disinfectant 20 is adaptable to be any suitable type, form and/or amount of disinfectant that can sterilize or substantially sterilize plastic, rubber, metal or other like materials. In an embodiment, the disinfectant 20 is composed of povidone iodine. It should be appreciated that the povidone iodine can be provided in any suitable form and/or amount thereof. In an embodiment, a povidone iodine gel may have been subjected to gamma irradiation, steam sterilization and/or ethylene oxide.

In another embodiment, the disinfectant is or includes iodine-containing antimicrobials. In a further embodiment, the disinfectant uses or includes a povidone iodine (not in gel form) that is or may be subjected to gamma irradiation and/or steam sterilization. In still another embodiment, the disinfectant is or includes betadine. It should be appreciated that the disinfectant 20 of the present invention can alternatively be any desired disinfectant known to those of skill in the art.

The body 14 of the cap 12 also in an embodiment defines internal threads 22 and external threads 24. In the illustrated embodiment, the internal threads 22 and external threads 24 reside on the same end of the cap 12. The purpose of the inner and outer threads will be shown below. It is important to note, however, that the relative relationship between the internal threads 22 and the external threads 24 is not important to the operation of the present invention. In general, the body 14 of the cap 12 enables the first member to move along the central axis of the body 14 via one of the set of threads. The body 14 of the cap 12 also enables a second member to move along the central axis of the body 14. It is not important which member moves by engaging the internal threads 22 and which member moves in the other direction by engaging the external threads 24. An important aspect of the present invention, rather, is that two separate members may move inward and outward relative to the body 14 of the cap 12.

The inner threads 22 and the outer threads 24 may have any thread pitch desired by the implementor of the present invention. In the illustrated embodiment, the external threads 24 are slightly tapered, for example, at about one degree. In an alternative embodiment, the threads are straight, such as in a lead screw or ball screw. In the illustrated embodiment, the external threads 24 enable one member to translate relative to another, wherein the member eventually bottoms out or has a limited range of travel with respect to the external threads 24. Likewise, the inner threads 22 may be straight threads that allow a member to rotate freely in and out of the body 14 or the inner threads 22 may be tapered such that the member bottoms out as it inserts into the body 14.

The body 14 defines a passage 26 that enables a medical fluid such as a dialysate to move from one end of the cap 12 to another. The passage 26 can alternatively be the opening defined by the inner threads 22 and does not have to include the reduced tubing piece illustrated as the passage 26 in FIG. 1A. The passage 26, however, is sized to have approximately the same inner diameter as the tubes or catheters carrying the dialysate back and forth from a dialysate container and the peritoneal cavity of the patient.

In the illustrated embodiment, the body 14 defines a housing 28 at an end opposing the internal and external threads 22, 24. The housing 28 is sized to hold a septum 30. The housing 28 is swaged to the septum 30 or otherwise holds the septum 30 in a snug manner. The septum 30 cannot move in either axial direction relative to the body 14. The body 14 defines an end wall 32 having a smaller inner diameter than that of the housing 28, which also holds the compressible septum 30 in place. A suitable adhesive may also be employed to hold the septum 30 within the housing 28.

In an embodiment, the septum 30 is cylindrical as is the body 14 and the connector 10 in general. However, the septum 30, the body 14, and the connector 10 can each have alternative shapes such as being square or rectangular.

The septum 30 in an embodiment is made of a compressible or rubber material. The septum can be made from any type of rubber, including any of the above listed rubbers. As is well known in the art, the septum 30 defines a slit (not illustrated) which enables a tube or other type of fluid communication member to pass through a back wall 34 of the septum 30. The septum 30 in the illustrated embodiment generally defines a cap or nut-shaped rubber or otherwise compressible piece having the back wall 34 and a cylindrical side wall 35 that extends from the back wall 34. The nut-shaped or cap-shaped septum in an embodiment is made as one piece, wherein the slit is made in the back wall 34. A tube or fluid communication member then inserts and resides inside a hollow chamber defined by the septum 30 and at some point is able to pass through the back wall 34.

In the illustrated embodiment, the connector 10 is configured so that the external threads 24 of the body 14 mate with internal threads of a shell 36. The shell 36 is a plastic or metal piece and may be of the same material as the body 14 of the cap 12. The shell 36 defines the internal threads 38 that mate with the external threads 24 of the body 14. The shell 36 can thus translate in either axial direction relative to the body 14 by rotating in a clockwise or counterclockwise direction about the body 14.

The shell 36 defines a tube or port 40, which in an embodiment is integrally formed with the shell 36, e.g., through an injection molding or blow molding process. The tube 40 extends inwardly into a cavity defined by the shell 36 and into the body 14 of the cap 12 through an opening defined by the end wall 32 of the body 14. The tube 40 also inserts into the cavity defined by the septum 30. When the shell 36 rotates about the outer threads 24 of the body 14 to a packaging position, an end 41 of the tube 40 abuts or is directly adjacent to the back wall 34 of the septum 30. For example, there may be a gap of about 0.010 in. (0.25 mm.) between the end 41 of the tube 40 and the back wall 34 of the septum 30.

The tube or port 40 also extends outwardly from the shell 36. The tube or port 40 sealingly connects to a tube (not illustrated) that runs to a dialysate container or a container housing the medical fluid that transfers through the connector 10 of the present invention. In an embodiment, the tube connecting to the dialysate bag press fits or sealingly fits over the port 40 in such a way that the dialysate does not leak from the interface of the flexible tube running to the dialysate container and the port 40. The tube of the dialysate bag can also connect to the port 40 via a solvent bond.

It should be appreciated that the dialysate is generally transferred back and forth, to and from, the dialysate container under its own weight and generally does not require an external pump or pressure system to drive the flow. Therefore, the fluid is not under substantial pressure and the seal required for the port 40 is not difficult to achieve. In an alternative embodiment, a hose clamp or other type of releasably fastenable device may be used to bolster the seal made between the flexible tube running to the dialysate bag and the port 40. Such interface is made readily and without requiring the patient or user to have an excessive amount of strength or to perform overly intricate operations.

A tip protector 42 fits over the shell 36 and at the same time fits into the interior cavity defined by the internal threads 22 of the body 14. The tip protector 42 is made in an embodiment of any of the plastic materials described above. The tip protector 42 defines a ring or handle 44 that enables the user or patient to remove the tip protector 42 from the shell 36 to begin using the connector 10. That is, the connector 10 is initially packaged with the tip protector 42. The first time the user or patient uses the tip protector 42, the user or patient removes the tip protector and discards it.

The tip protector 42 serves a number of purposes in protecting the connector 10 prior to use. The tip protector 42 provides a microbial barrier. The tip protector 42 disallows bacteria and other harmful airborne agents from entering the body 14 of the cap 12 prior to use. Just before attaching the cap 12 to a mating connector (see mating connector 60 in FIGS. 2 through 7), the patient or operator removes the tip protector 42. In this way, the inside of the body 14 of the cap 12 is only exposed to open air for a very short amount of time.

In an embodiment, for example, when the connector 10 is to be used for CAPD, the tip protector 42 also sets the shell 36 at the appropriate distance relative to the body 14 for packaging the connector 10. That is, the tip protector 42 helps to set the end 41 of the tube 40 of the shell 36 directly adjacent to the back wall 34 of the septum 30.

Prior to use, the tube 40 does not insert into or open up the slit (not illustrated) in the back wall 34 of the septum 30. However, it is desirable not to have the end of the tube or port 40 too far away from the back wall 34 of the septum 30 upon packaging the connector 10 for a couple of reasons. First, it is desirable to package the connector 10 in as small a space as possible. If the connector 10 is packaged so that the end 41 resides away from the back wall 34, then the connector 10 is longer in an axial direction than it needs to be. Second, it is desirable not to make the user or patient rotate the shell 36 more than is necessary to insert the tube 40 through the slit of the back wall 34 of the septum 30 to begin using the connector 10.

FIGS. 1A and 1B illustrate that the tip protector 42 in an embodiment defines threads 46 that engage some of the internal threads 38 of the shell 36. The shell 36 only threads into the tip protector 42 so far before the shell 36 bottoms out against a cylinder 48 defined by the tip protector 42. FIG. 1B illustrates that in an embodiment, the outside of the shell 36 includes a taper 35 at the end of the portion of the shell 36 defining the threads 38. As the tip protector 42 threads into the shell 36, the taper 35 increasingly presses against the inside of the cylinder 48. In an embodiment, the cylinder 48 of the tip protector 42 defines a stepped portion 47 that facilitates the engagement between the taper 35 of the shell 36 and the tip protector 42.

Thus, when the connector 10 is packaged, the tip protector 42 can be placed against or abutted against the body 14 of the cap 12 before the shell 36 threads onto the body 14 and onto the threads 46 of the tip protector 42. The shell 36 threads over the external threads 24 of the body 14 and passes or translates past the body 14 a desired distance defined by the threads 46 of the tip protector 42. It is at this point that the end 41 of the tube 40 abuts or is directly adjacent to the end wall 34 of the septum 30.

It should be appreciated that the cylinder 48 of the tip protector 42 is not threaded and does not threadingly engage the shell 36 so that the cylinder 48 simply slides over and translates relative to the shell 36. It should also be appreciated that to remove the tip connector 42, the user holds the shell 36 and rotates the ring 44 a number of turns.

FIG. 1C illustrates an alternative embodiment that is used, for example, when the connector 10 performs APD. The tip protector 42 simply slides and possibly slightly press fits onto or into the body 14 of the cap 12. Here, the tip protector 42 does not define the threads 46. The shell 36 may or may not be tapered and may contain a stepped member 37, wherein the member 37 is intended to slightly frictionally engage the inner wall of the cylinder 48. The internal threads 38 of the shell 36 stop before reaching the inner portion 39 of the shell 36 that abuts the tip protector 42.

When the connector is initially packaged, the body 14 cannot move relative to the shell 36 until the tip connector 42 is removed. This is important to ensure that the seal 18 is not ruptured or displaced prior to using the connector 10. The tip protector 42 also includes an inner extension 50 that extends into the chamber created by the internal threads 22 of the body 14. The extension 50 extends so that it abuts or is directly adjacent to the seal 18. This ensures that prior to use, the seal 18 does not loosen and move away from the receptacle 16 to thereby create a leaky connector 10. Thus, it should be appreciated that the tip connector 42 enables the connector 10 to be handled and shipped without destroying the seal 18 and/or losing the disinfectant 20 maintained by the seal 18.

Figure 2:
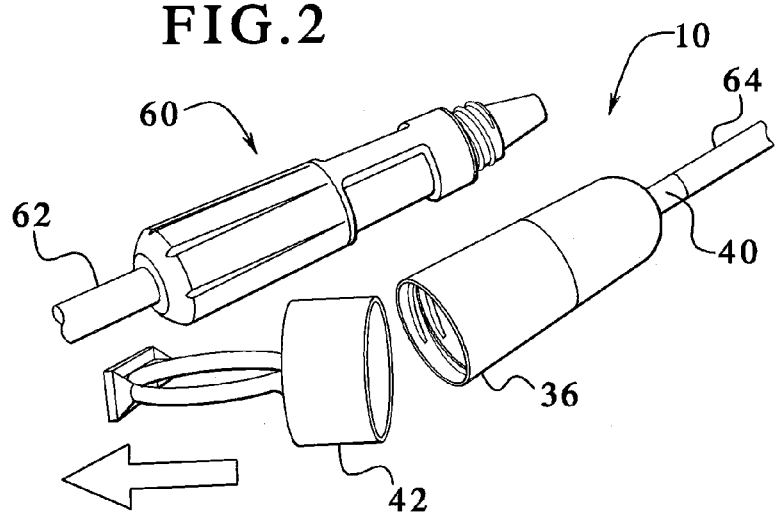
FIG. 2 is a perspective view illustrating a part of the process for connecting the connector and cap of the present invention to a transfer set, which connects a catheter to a patient.
Figure 3:
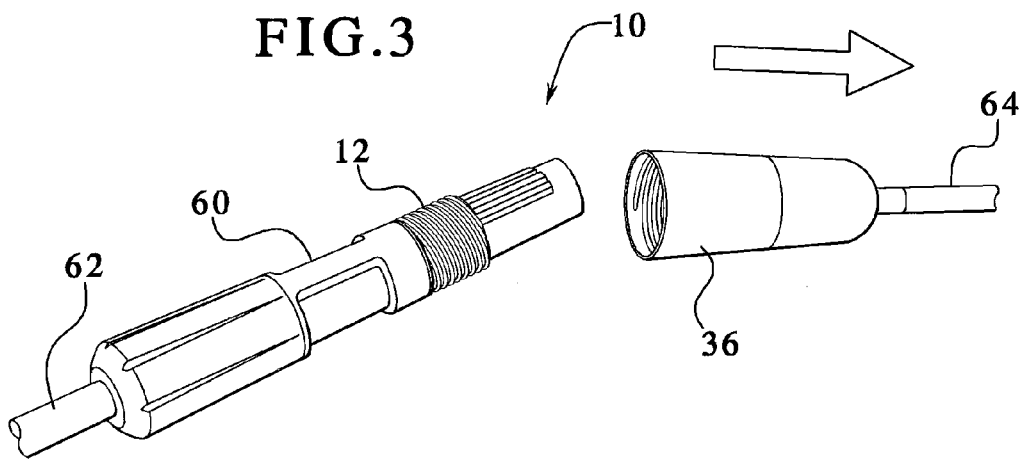
FIG. 3 is a perspective view illustrating another part of the process for connecting the connector and cap of the present invention to a transfer set, which connects a catheter to a patient.

Referring now to FIGS. 2 and 3, one embodiment for connecting the connector 10 of the present invention to a mating connector 60 is illustrated. The connector 10 may be adapted to operate with many different types of connectors or devices that provide access to a catheter that inserts into the peritoneal cavity of the patient. In an embodiment, the connector 10 is adapted to attach to a transfer set that is illustrated in FIG. 2 as the connector 60. The transfer set in one embodiment is a MiniSet™ manufactured by BAXTER INTERNATIONAL INC. Although the MiniSet™ 60 is one operable embodiment of the transfer set or catheter device, the connector 10 can operate with any type of device that couples to a tube or catheter, which inserts into the patient's peritoneal cavity.

In FIG. 2, the tip protector 42 is unsecured or removed from the shell 36 of the connector 10. The port 40 of the shell 36 of the connector 10 is illustrated as sealingly connecting to a flexible tube 64 that runs to the dialysate container or bag.

FIG. 3 illustrates that after inserting the connector 10 onto the connector or transfer set 60, the shell 36 connected to the tube 64 threads off of and away from the cap 12. The connector 10 threads onto the connector or transfer set 60 using the internal threads 22 defined by the body 14 of the cap 12, which are exposed when the tip protector 42 is removed.

FIG. 3 illustrates a point in the process when the patient has completed the transfer of the dialysate from the dialysate container into the peritoneal cavity, or FIG. 3 illustrates a point in the process when the patient or user has finished draining spent dialysate from the peritoneal cavity into the dialysate container. In either situation, when the shell 36 threads off of the container 10, the cap 12 of the container 10 remains fixed to the connector or transfer set 60 and thereby caps off the transfer set 60. In this manner, because the sterility of cap 12 is maintained and cap 12 remains functional, a separate cap which would normally have to be taken off and re-placed onto the transfer set 60 before and after each use is no longer necessary.

Figure 4:
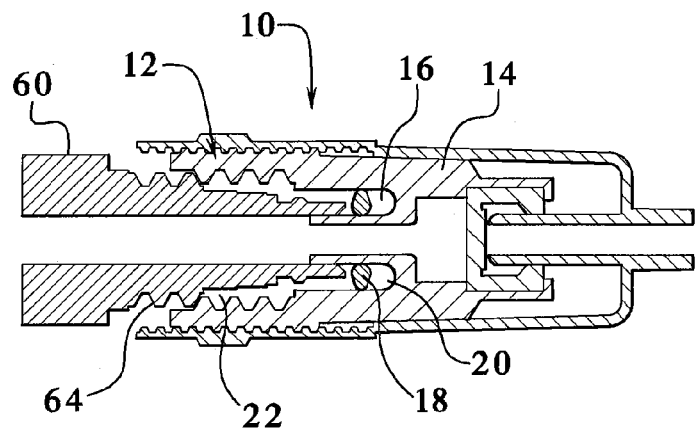
FIG. 4 is a schematic sectional view illustrating one step for using the connector and cap of the present invention to insert and/or remove a medical fluid into/from a patient.

Referring now to FIGS. 4 to 7, one embodiment of a method for removing spent dialysate and inserting new dialysate into a patient in a substantially sterilized environment is illustrated. FIG. 4 illustrates a point in the process when the tip protector 42 has been removed and the transfer set or connector 60 is ready to be connected to the connector 10. At this point, the connector or transfer set 60 has not engaged the seal 18 to thereby rupture or displace the seal, which displaces the disinfectant 20. The connector or transfer set 60 includes external threads 64 that mates with the internally facing threads 22 of the body 14 of the cap 12.

Figure 5:
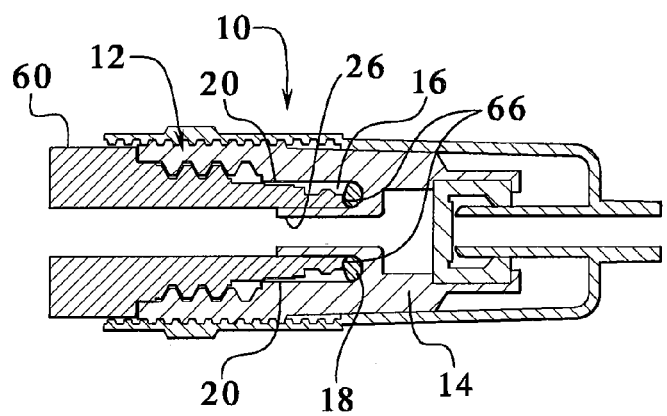
FIG. 5 is a schematic sectional view illustrating another step for using the connector and cap of the present invention to insert and/or remove a medical fluid into/from a patient.

When the user or patient desires to connect the catheter from the peritoneal cavity to the connector 10, the user or patient threads the connector or transfer set 60 (connecting to the catheter extending to the peritoneal cavity) into the body 14 of the cap 12 so that ends 66 of the connector transfer set 60 engage the seal 18 and either move it or rupture it (best seen in FIG. 5). That is, the ends 66 apply a translational force to the seal 18 which causes the seal 18 to compress against the disinfectant 20. Eventually, as the user screws the connector 60 into the body 14, the pressure becomes too much for the seal to handle, whereby the seal either moves so that the disinfectant leaves the receptacle 16 and squirts out around the seal 18 and the ends 66 pierce, or the seal ruptures (thin sheet seal embodiment described above) and the disinfectant 20 runs out over the external threads 64 of connector 60.

In the illustrated embodiment, the seal 18 remains intact but moves or displaces the disinfectant 20 to run out over the outside of the threads 64 of the connector 60, so that microorganisms contained thereon are substantially destroyed. The seal 18 as illustrated may be made in a teardrop-type shape wherein the blunt end of the teardrop has more sealing force than the tapered or sharper end of the seal 18. In this manner, the sharper or tapered end may slightly deform as the blunt end is dragged along the surface of the receptacle 16.

The mating connector 60 in an embodiment is sized to engage and slide along the passage 26 of the body 14. This also aids in dispersing the disinfectant 20 onto the outside of the mating connector 60 to disinfect the engaging threads. That is, the disinfectant will take the path of least resistance and tend to move into the open cavity defined between the outside of the connector 60 and an inner wall of the body 14, rather than squeezing through the friction fit between the inner opening of the connector 60 and the passage 26.

Figure 6:
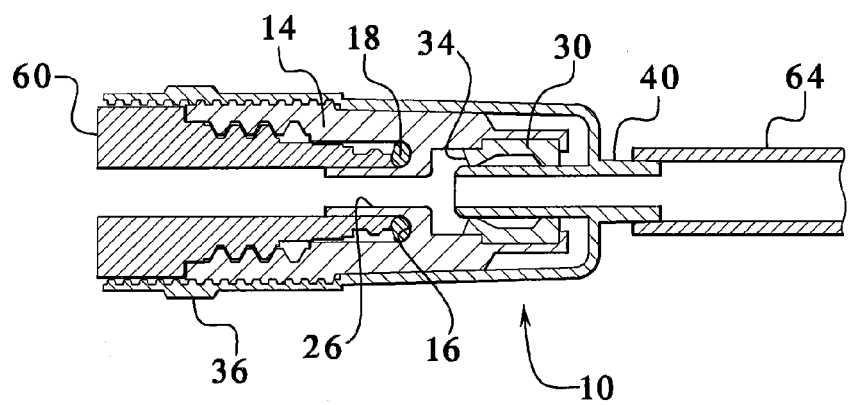
FIG. 6 is a schematic sectional view illustrating a further step for using the connector and cap of the present invention to insert and/or remove a medical fluid into/from a patient.

Referring now to FIG. 6, after the mating connector or transfer set 60 bottoms out against the body 14, i.e., pushes the seal 18 all the way against the receptacle 16 of body 14. The assembly of the connector 10 to the mating connector 60 is now complete, so that the sealed end of the body 14 made by the slit septum 30 can be unsealed or opened. To break the seal of the septum 30, the user or patient rotates the shell or shell 36 relative to the body 14 wherein the threads of the shell 36 turn against the threads of the body 14. The shell 36 thereby translates towards the mating connector 60, so that the tube or port 40 of the shell 36 pierces through the back wall 34 of the septum 30 and through the slit defined by the back wall 34. At this point, fluid communication exists between the peritoneal cavity of the patient and the dialysate bag.

Thus, at the point illustrated in FIG. 6, the dialysate fluid may flow in either direction. That is, if the patient is removing spent dialysate from the peritoneal cavity, the dialysate fluid can flow from the catheter in the cavity into the mating connector 60, through the passage 26 of the body 14, out the port 40 and into the flexible tube 64 running to the dialysate container or bag.

In CAPD, to remove the spent dialysate from the peritoneal cavity, the user or patient typically opens a clamp on the upstream side of the mating connector 60 or integrally formed with the mating connector 60, wherein the spent dialysate runs into an awaiting container. The flex tube 64 typically runs to a "Y" connection, wherein one leg extends to the spent dialysate container and another leg extends to a new dialysate bag. When the old dialysate has been drained into the spent bag, the operator opens a fill-bag clamp that enables the new dialysate to run from the flexible tube 64, to the port 40, through the septum 30, through the passage 26, into the internal diameter of the mating connector 60 and into the catheter leading into the peritoneal cavity. With APD, one or more pumps automatically pull the spent dialysate from the patient's peritoneal cavity and places fresh dialysate into same.

FIGS. 4, 5 and 6 illustrate one complete cycle of flushing old or spent dialysate and replenishing new dialysate into the peritoneal cavity. With both CAPD and APD, the cycle is repeated a number of times. Obviously, many other different types of medical fluids may be substituted for the dialysate described herein, wherein a number of medical procedures may be performed using the connector 10 having the cap 12 of the present invention.

Figure 7:
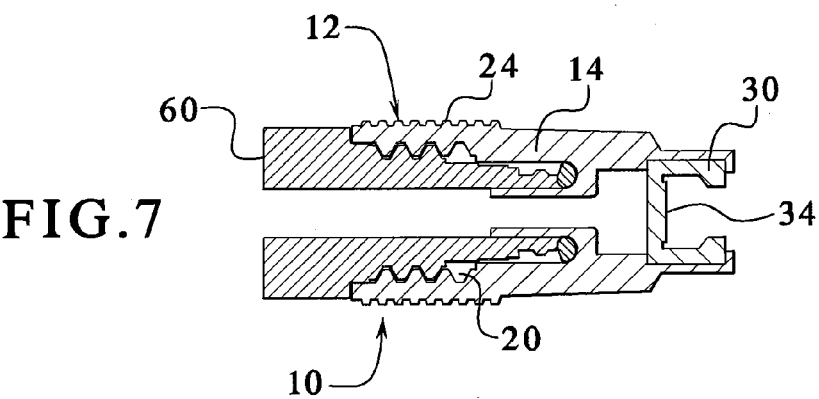
FIG. 7 is a schematic sectional view illustrating still another step for using the connector and cap of the present invention to insert and/or remove a medical fluid into/from a patient.

Referring now to FIG. 7, when the transfer of fluids has been exchanged, the user or patient removes the shell 36 from the cap 12, so that the tube 40 of the shell 36 removes from the septum 30. When removed, the slit in the wall 34 of the septum 30 closes and the end of the body 14 is once again sealed. The body 14 remains in the threaded position with respect to the mating connector 60, so that the disinfectant 20 is maintained between the mating threads and the open area between the mating connector 60 and the body 14.

FIGS. 8 to 11 illustrate a container assembly 100 of the present invention for providing a medical device, in this case a fresh sterile cap 12 during treatment or interruption of treatment. As used herein the term medical device includes needles, medical connectors, plugs, and the like. The container assembly 100 includes a lid 102 and a container 104, whereby the new cap 12 is designed to fit securely within the container 104. The secure fit prevents the cap 12 from moving since movement may cause the seal 18 to rupture or be displaced prior to use, thus releasing the disinfectant 20 maintained by the seal 18 (see seal 18 FIG. 9). Generally, the components are made of a plastic material such as polyethylene, polypropylene, nylon, polystyrene, polyester, PVC, a blend of various plastics or any other plastic or synthetic material that is capable of being washed and sterilized or substantially sterilized, particularly by gamma sterilization processes.

Figure 8:
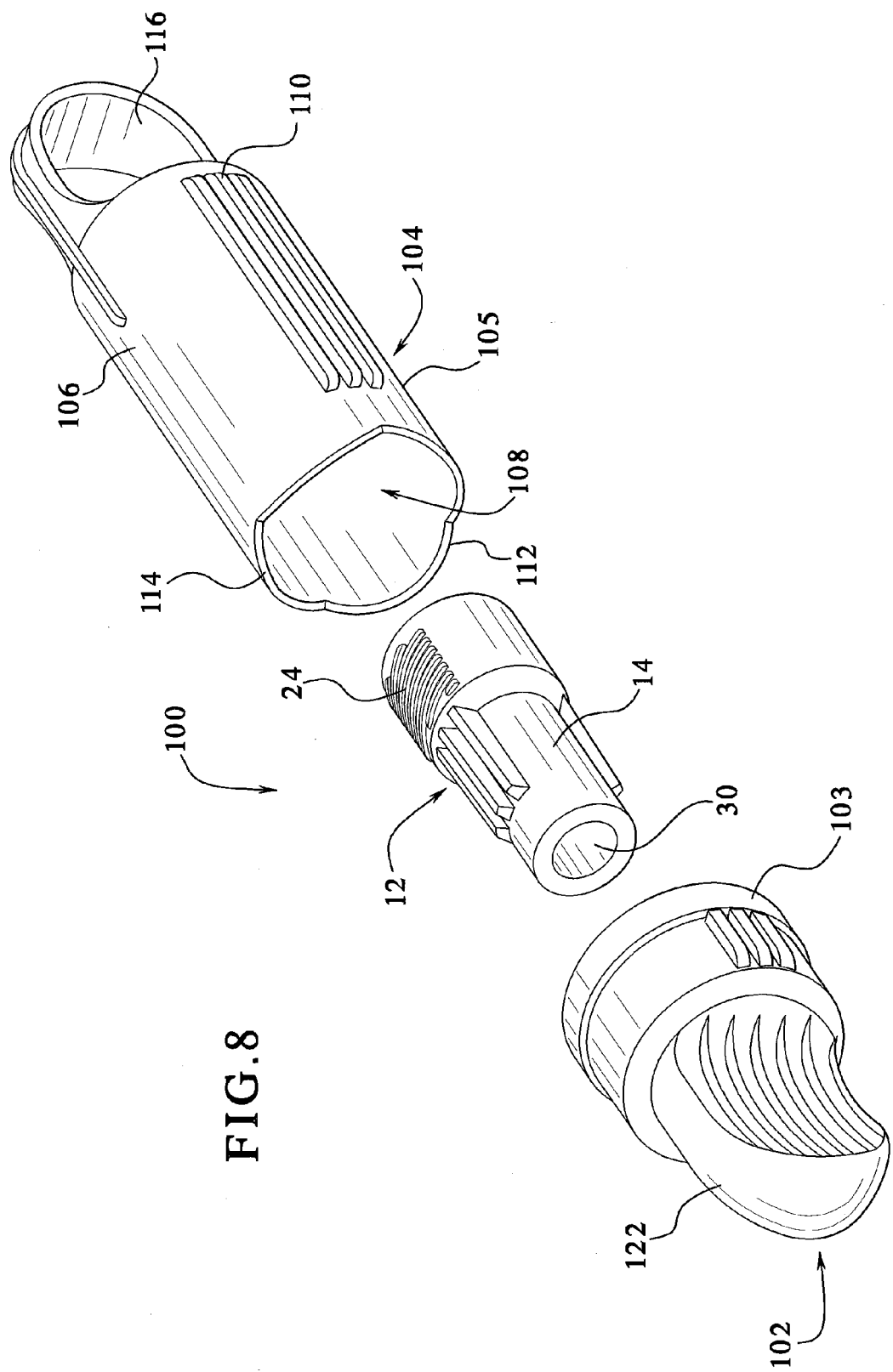
FIG. 8 is a perspective view of one embodiment of the container, the medical device housed therein, and lid therefore of the present invention.

The container 104 includes a container body 106 that is injection molded or blow molded to define a desired shape. Although FIG. 8 shows one embodiment of the container body 106 and the lid 102, the container body 106 and the lid 102 may be made in a variety of different shapes and sizes to mate with and/or work with various systems for introducing medical fluids into a patient. The various systems can be provided by other manufacturers or by the assignee of this invention. In one embodiment, the container 104 and lid 102 define the following components or features.

The container body 106 defines a passage 108 having a bottom surface 110 and an opening 112 opposite the bottom surface 110. The opening 112 is sized to allow a cap 12 to easily fit within the container body 106. The container body 106 is tapered toward the bottom surface 110 in such a manner that the circumference of the bottom surface 110 is smaller than the circumference defined by the opening 112.

This design allows the container body 106 to fit over the connector 10 when it is being used, the details of which are described in more detail below.

In a preferred embodiment, the container body 106 will generally be clear so that a patient using the container 104 can see the cap 12 housed within the container body 106, although the container body 106 may also have color and solid portions as well.

Generally, the container body 106 will define a collar 114 at the opening 112. The collar 114 will preferably have a cam edge geometry which can be a saw tooth configuration, a curved surface, or the like. In the illustrated embodiment, the cam edge geometry has a substantially saw tooth configuration. The geometry of the collar 114 acts as a cam in order to initiate cam-follower action or cantilever action between the lid 102 and the container body 106. The cam-follower action or cantilever action allows for an easy snap release or separation of the lid 102 from the container body 106 when a patient or user twists the lid 102. The cam-follower action also provides for a very tight seal so that the user or patient knows that the container lid is completely closed. The outer surface of the container body also includes a section with a slightly raised surface 105 which acts as an engagement interface for the lid 102. This slightly raised surface 105 allows for the snap fit between the lid 102 and container body 106.

In an embodiment, the container 104 may also include an integrally formed handle 116 formed along the bottom surface 110 of the container body 106. In the illustrated embodiment the handle 116 is ring shaped, although other configurations and shapes may also be used. The handle 116 is designed so that a patient can easily grasp the container 104 and remove the lid 102 to access the cap 12 during treatment or interruption of treatment. The position of the handle 116 allows the container 104 to be used in such a fashion so that the hands of the patient or user never come in close proximity to the cap 12, thus reducing the possibility of contamination.

Figure 9:
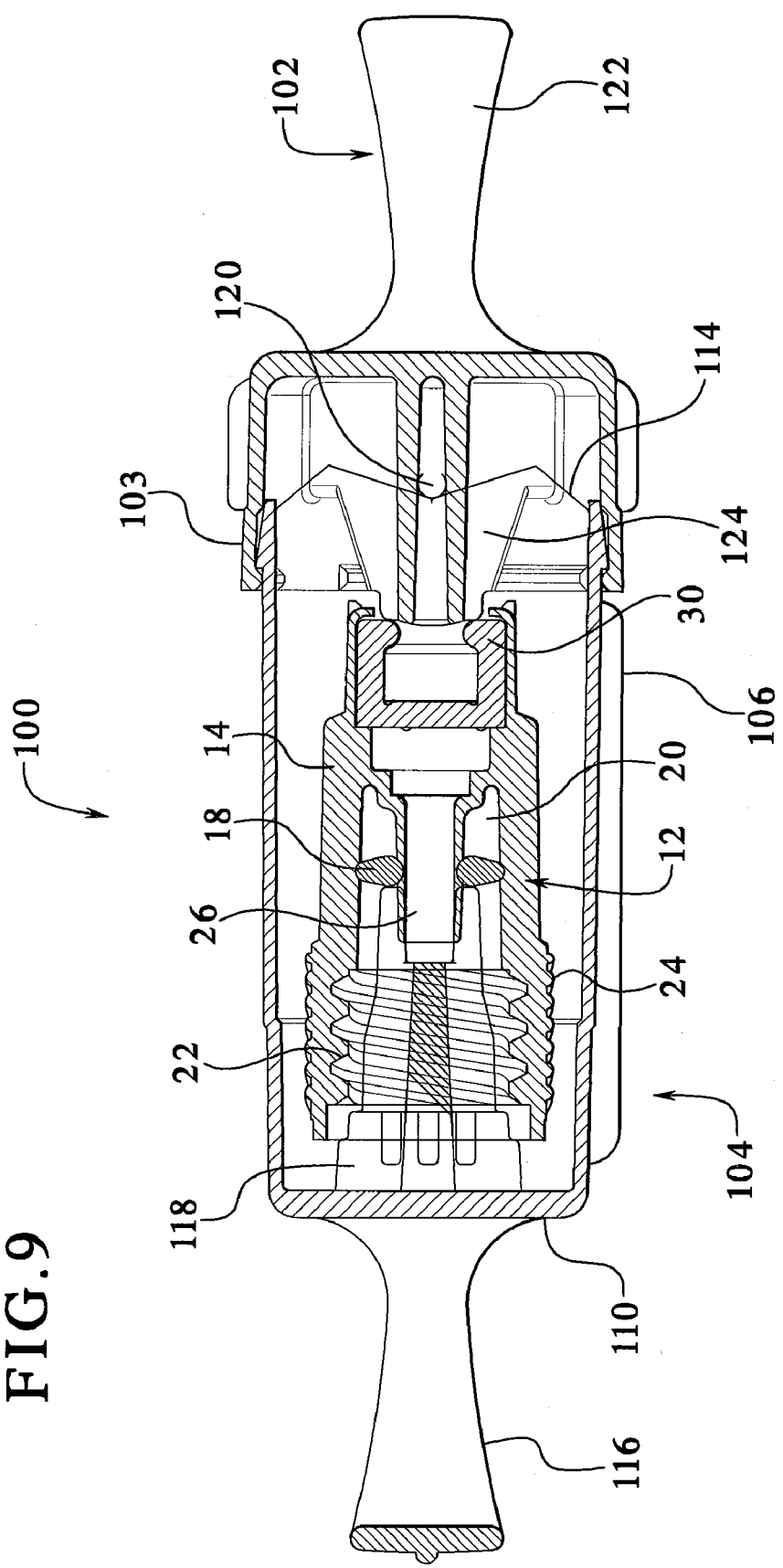
FIG. 9 is a schematic sectional view showing an embodiment of an interface between the container, the medical device and the lid.
Figure 10:
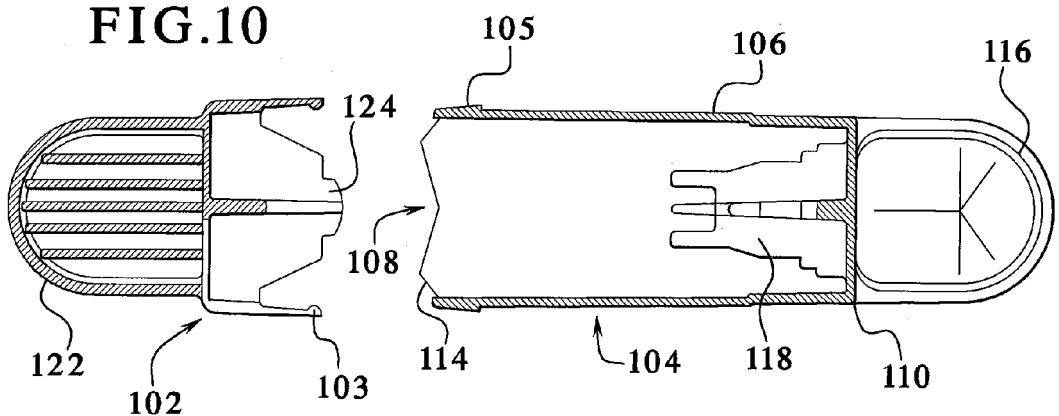
FIG. 10 is a schematic sectional view showing another embodiment of an interface between the container and the lid.

FIGS. 9 and 10 illustrate the bottom surface 110 of the container body 106. In one embodiment, the bottom surface 110 includes a securing mechanism 118 for holding the cap 12 in place when it is disposed within the container 104. In the illustrated embodiment, the securing mechanism 118 is defined by an integrally formed molding on the bottom surface 110, however various other features and mechanisms may also be used for securing the cap body 14. The securing mechanism 118 is designed to fit into the interior cavity of the cap 12 defined by the internal threads 22 of the body 14. This interface aligns cap 12 within the container body 106 during assembly and prevents disengagement of the cap 12 from the container body 106 during transport or handling by the patient or user. The securing mechanism 118 is also sized such that it does not interfere with or engage seal 18 of the cap 12. This prevents the seal 18 from being inadvertently ruptured or the disinfectant 20 housed therein from being released prior to use.

Referring still to FIGS. 9 and 10, one embodiment of a lid 102 of the present invention is illustrated. The lid 102 is preferably made from plastic material softer than the container 104, but may also be made of any of the plastic materials described above. The lid 102 includes an outer surface 103 which is designed to fit securely over the collar 114 of the container 104. The outer surface 103 engages the raised surface 105 on the exterior surface of the container body 106. As the lid 102 is pushed further toward the container body 106 a tight snap fit seal is created. The snap fit prevents the possibility of the lid 102 inadvertently being removed from the container 104 prior to use.

At least one follower 120 is provided on an interior surface of the lid 102 for engaging the saw tooth configuration of the collar 112. The lid 102 may also include an integrally formed handle 122 so that the lid 102 can easily be turned and removed from the container body 106 thus enabling a user or patient to access and use the cap 12 and container body 106 assembly, as described in detail below. In the illustrated embodiment, the handle 122 is relatively flat shaped, however it is envisioned that other configurations and shapes may also be used.

In a preferred embodiment, the lid 102 may also include a downwardly extending projection 124 for engaging and holding the cap 12 in place when it is disposed within the container 104. In this regard, the lid 102 will work in conjunction with the securing mechanism 118 located on the bottom surface 110 in order to securely maintain the cap 12 within the container 104. In an alternative embodiment, the downwardly extending projection 124 also acts as a tip protector and actually engages the septum 30 of the cap 12 to act as a microbial barrier, thus preventing contamination of the cap 12 prior to removal of the lid and use.

Figure 11:
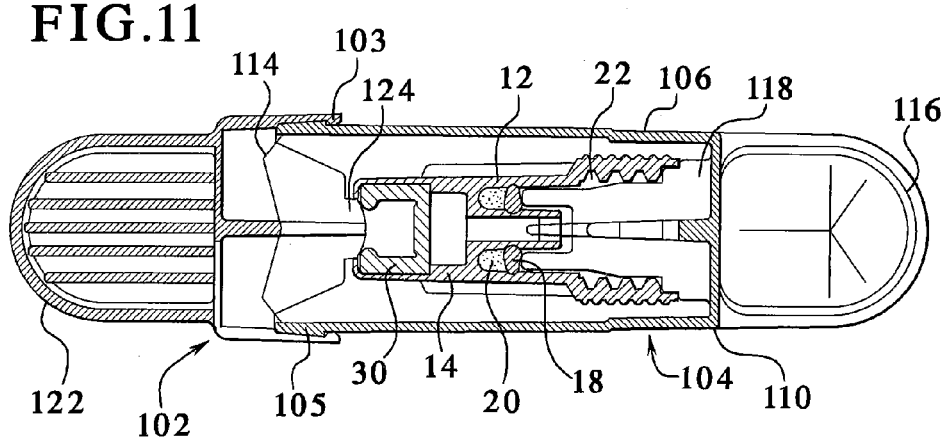
FIG. 11 is a schematic sectional view showing an embodiment of an interface between the container, the medical device and the lid.
Figure 12:
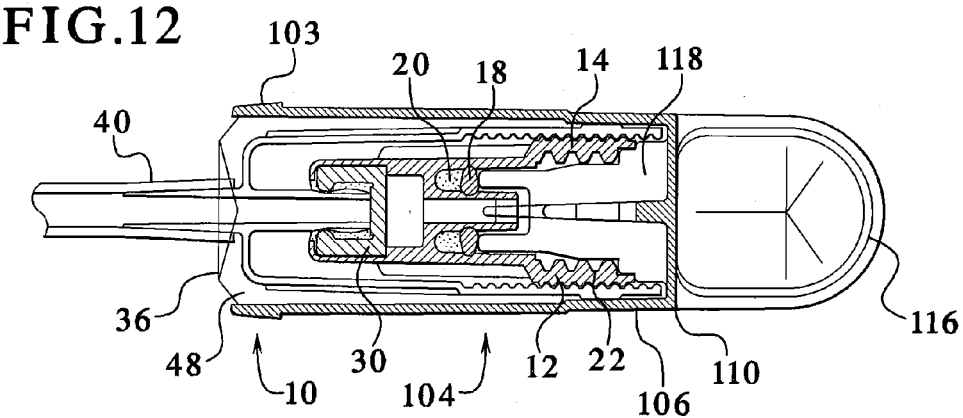
FIG. 12 is a schematic sectional view illustrating a part of the process for connecting the container and medical device of the present invention to a connector, which connects to a dialysate line.

Referring now to FIGS. 11 and 12, another illustration of the complete assembly of the container 100 is shown, as well as an illustration of a connection of the container 104 and cap 12, after the lid 102 is removed, to the shell 36 and tube 40 of connector 10 during treatment or treatment interruption. In the illustrated embodiment, the container body 106 fits over the exterior surface of the shell 36. The fact that the container body 106 is tapered toward the bottom surface 110 insures a secure interference fit between the container body 106 and the shell 36. While the container body 106 is designed to fit over the shell 36, the cap 12 is designed to be inserted and turned inside the shell 36. The cap 12 interfaces with the shell 36 in substantially the same way as described previously. The container body 106 and cap 12 are left attached to the shell 36 to protect the shell 36 from contamination and to create a torture pass during treatment or treatment interruption.

When it is time to begin using the cap 12, the container body 106 is pulled away from the cap 12, which remains attached to the shell 36, and discarded. The patient or user may then attach the mating connector (see mating connector 60 in FIGS. 2 through 7) to resume treatment. In this way, the body 14 of the cap 12 and mating connector 60 are only exposed to open air for a very short amount of time.

Figure 13F:
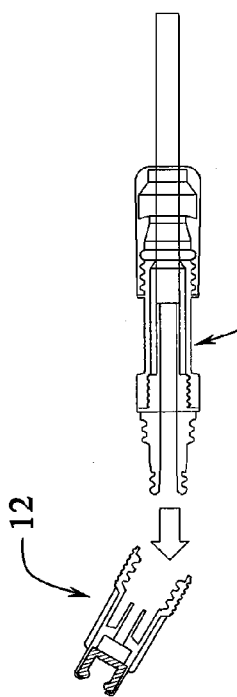
FIG. 13F is a schematic sectional view illustrating still another step for using the container and device of the present invention to maintain a sterile connection during treatment.
Figure 13G:
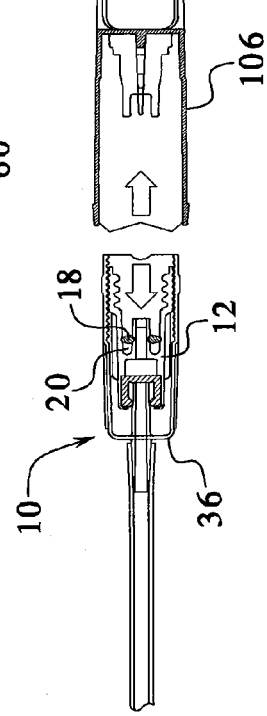
FIG. 13G is a schematic sectional view illustrating still another step for using the container and device of the present invention to maintain a sterile connection during treatment.
Figure 13H:
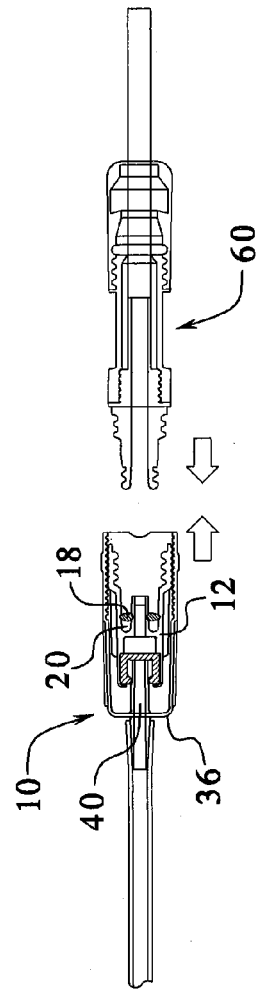
FIG. 13H is a schematic sectional view illustrating still another step for using the container and device of the present invention to maintain a sterile connection during treatment.
Figure 13I:
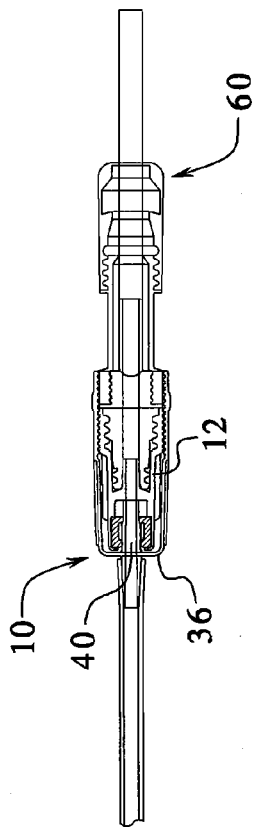
FIG. 13I is a schematic sectional view illustrating still another step for using the container and device of the present invention to maintain a sterile connection during treatment.

Referring now to FIGS. 13A to 13I, one embodiment of a method for using the container assembly of the present invention to maintain a substantially sterilized environment is illustrated. FIG. 13A illustrates a point in the process when the mating connector or transfer set 60 is connected to the connector 10. At this point, fluid communication exists between the peritoneal cavity of the patient and the dialysate bag. Upon completion of treatment, the mating connector 60 including cap 12 is disconnected from the connector 10. During this step, connector 10 is left unprotected and exposed to open air, while mating connector 60 is protected from contamination by cap 12.

In order to maintain a sterile connection, the user or patient will then obtain the container assembly 100 and remove and dispose of the lid 102. The patient or user will then push the container body 106 over the shell 36, while at the same time force the cap 12 into the shell 36. By forcing cap 12 into the shell 36, the septum 30 of cap 12 will engage the tube 40. By placing the container body 102 over the unprotected connector 10, the patient or user is reducing the risk of contamination of the line during breaks in treatment. At this point, both lines are now fully protected from contamination allowing the patient to walkaway without having to perform any additional steps.

When the patient or user returns to reconnect and resume treatment, the patient will remove and discard old cap 12 from mating connector 60. The patient also removes the container body 106 from connector 10 leaving cap 12 in the threaded position with respect to shell 36 described in detail above. Accordingly, reconnecting the mating connector 60 and the connector 10, will rupture seal 18 of cap 12 and disperse the disinfectant 20 over the assembly, further sterilizing the line in a similar fashion as described above. The patient will then be ready to fully resume treatment. The advantages offered by the present system are that the patient can readily connect and disconnect the treatment lines without having to perform overly complicated steps and the possibility of contamination is drastically reduced.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A container for a medical device comprising:
   a body defining a passage, the body having a bottom surface and an edge opposite the bottom surface, the bottom surface having an integrally formed securing mechanism releasably retaining the medical device securely in the body, the edge defining a first cam-follower member, the medical device is a cap for use in making a resealable fluid path wherein one end of the cap is operatively connectable to a peritoneal cavity of a patient and another end of the cap is operatively connectable to a fluid container; and
   a lid defining a second cam-follower member, the lid and the body being configured to provide a snap release of the lid from the body in response to a cam-follower action between the first and second cam-follower members.

2. The container of claim 1, wherein the body includes a collar defining the opening, the collar having a continuous cam edge geometry.

3. The container of claim 2, wherein the lid includes a follower for engaging the cam edge geometry, so that turning the lid will push the lid away from the container.

4. The container of claim 1, wherein the body includes a collar which engages and secures the lid by means of a snap mechanism.

5. The container of claim 1, wherein the body includes an integrally formed handle attached to the bottom surface of the body.

6. The container of claim 1, further comprising a medical device disposed within the container.

7. The container of claim 1, wherein the medical device further comprises a seal disposed within an interior surface, the seal maintaining a disinfectant.

8. The container of claim 7, wherein the disinfectant comprises povidone iodine.

9. The container of claim 1, wherein the lid includes a downwardly extending projection for engaging and holding the medical device in place.

10. The container of claim 1, wherein the integrally formed securing mechanism engages an interior surface of the medical device so that the device is held securely within the container.

11. The container of claim 1, wherein the lid includes an integrally formed handle.

12. The container of claim 1, wherein the lid includes a tip protector for engaging a slit septum of the medical device.

13. The enclosure of claim 1, wherein the first cam-follower member forms a cam surface and the second cam-follower member forms a follower surface.

14. An enclosure for a medical device comprising:
   a body defining a passage, the body including a bottom surface having an integrally formed securing mechanism releasably retaining the medical device securely in the body, the medical device is a cap for use in making a resealable fluid path wherein one end of the cap is operatively connectable to a peritoneal cavity of a patient and another end of the cap is operatively connectable to a fluid container;
   a lid, the lid and the body being configured to provide a snap release of the lid from the body in response to a cantilever action between the body and the lid;
   an edge including projections and undulations located on one of the body and the lid;
   a follower defined on the other of the body and the lid; and
   wherein the cantilever action is caused by a movement of the edge relative to the follower.

15. The enclosure of claim 14, wherein the projections and undulations form a saw-tooth configuration.

16. The enclosure of claim 14, wherein the body includes a handle arranged to extend substantially along the central axis.

17. The enclosure of claim 14, wherein the edge having the projections and undulations is located on the body.

18. The enclosure of claim 17, wherein the cap includes a slit septum.

19. The enclosure of claim 18, wherein slit septum is configured to engage a downwardly extending projection formed within the lid.

20. The enclosure of claim 17, wherein the cap includes an interior surface configured to include a seal.

21. The enclosure of claim 20, wherein the seal supports a disinfectant.

22. A medical component enclosure, the enclosure comprising:
   a body extending along a central axis, the body having an open end that includes an edge having a continuously changing geometry extending in a direction substantially parallel to the central axis; and
   a lid sized to cooperate with the open end of the body to form a seal therebetween, wherein the edge is configured such that the lid translates with respect to the open end of the body in response to a twisting force to disengage the seal and allow access to a medical component releasably retained by the body, the medical component is a cap for use in making a resealable fluid path wherein one end of the cap is operatively connectable to a peritoneal cavity of a patient and another end of the cap is operatively connectable to a fluid container.

23. The enclosure of claim 22 further comprising a securing mechanism carried within the body, the securing mechanism aligned substantially along the central axis of the body.

24. The enclosure of claim 22, wherein the lid includes a follower surface configured to engage the continuously changing geometry of the edge when the seal is disengaged.

25. The enclosure of claim 22, wherein the continuously changing geometry includes a saw-tooth configuration.

* * * * *